United States Patent [19]
Magni et al.

[11] Patent Number: 5,986,142
[45] Date of Patent: Nov. 16, 1999

[54] PROCESS FOR PREPARING BICYCLOHEPTANAMINE COMPOUNDS

[75] Inventors: Ambrogio Magni, Osnago; Giovanni Signorelli, Milan, both of Italy

[73] Assignee: Poli Industria Chimica SpA, Milan, Italy

[21] Appl. No.: 08/935,812

[22] Filed: Sep. 23, 1997

[51] Int. Cl.$^6$ .................................................. C07C 211/34
[52] U.S. Cl. .......................... 564/460; 564/457; 564/458
[58] Field of Search .................................. 564/448, 457, 564/458, 460

[56] References Cited

U.S. PATENT DOCUMENTS

| | | | |
|---|---|---|---|
| 2,831,027 | 4/1958 | Pfister et al. | 260/563 |
| 2,972,631 | 2/1961 | Bain . | |
| 3,304,167 | 2/1967 | Buntin . | |
| 3,514,486 | 5/1970 | Hartzler . | |
| 3,717,650 | 2/1973 | Herr et al. . | |
| 3,884,976 | 5/1975 | Bernauer et al. . | |
| 4,053,511 | 10/1977 | Hoffmann . | |
| 4,087,551 | 5/1978 | May . | |
| 4,837,218 | 6/1989 | Olney . | |
| 4,898,888 | 2/1990 | Baldone . | |
| 5,284,976 | 2/1994 | Brown . | |

FOREIGN PATENT DOCUMENTS

| | | | |
|---|---|---|---|
| 0579260 A1 | 1/1994 | European Pat. Off. | A61K 31/00 |
| WO 96/01050 | 1/1996 | WIPO | A01N 33/12 |

OTHER PUBLICATIONS

Luskin, L.S. et al., "tert–Carbinamines. V. The Addition of Isothiocyanic Acid to Camphene," *J. Org. Chem.* 21:1430–1431 (1956).

Stein, G.A. et al., "The reaction of camphene with hydrogen cyanide," *J. Am. Chem. Soc.* 78:1514–1515 (1956).

Stone, C.A. et al., "Chemistry and Structure Activity Relationships of Mecamylamine and Derivatives," *J. Med. Pharm. Chem.* 5(4):665–690 (1962).

Suchocki, J.A. et al., "Synthesis of 2–exo–and 2–endo–Mecamylamine Analogues. Structure–Activity Relationships for Nicotinic Antagonism in the Central Nervous System," *J. Med. Chem.* 34:1003–1010 (1991).

CA:116:152086 abs of SU1671559 Aug. 1991.

CA:127:262429 abs of Synlett by Crousse (8) pp. 992–994 Apr. 1997.

CA:83:28678 ab of J Polym Sci, Polym Chem ED by Cohen 13 (3) pp. 745–8 1975.

CA:81:77581 abs of J Chem Soc Chem Comm by Butterick (8) pp. 307–8 1974.

*Primary Examiner*—Gary Geist
*Assistant Examiner*—Jean F Vollano
*Attorney, Agent, or Firm*—Townsend and Townsend and Crew LLP

[57] ABSTRACT

The present invention provides a process for preparing compounds of Formula I:

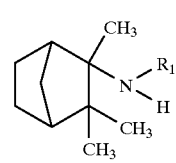

wherein $R_1$ is methyl by reduction of a camphene intermediate with a reducing agent.

5 Claims, No Drawings

PROCESS FOR PREPARING BICYCLOHEPTANAMINE COMPOUNDS

FIELD OF THE INVENTION

The present invention relates to methods of preparing useful pharmaceutically active agents and more particularly to methods of preparing bicycloheptan-amine compounds having pharmaceutical activity.

BACKGROUND OF THE INVENTION

Pharmaceutically active bicycloheptan-amines, including mecamylamine are useful for the treatment of hypertension in humans, and as ganglion blockers. Mecamylamine reduces blood pressure in both normotensive and hypertensive patients.

Conventionally, mecamylamine has been produced by the reduction of 3-formamidoisocamphane with lithium aluminum hydride. This technique is described in U.S. Pat. No. 2,831,027 to Pfister, III, et al. Another method for preparing mecamylamine is discussed in Great Britain Patent No. 856,862 to Lepetit et al. According to this method, mecamylamine is produced from 3-aminoisocamphane.

There remains a need in the art for methods of producing pharmaceutically active bicycloheptan-amines. There remains a need in the art for commercially viable methods of preparing pharmaceutically active bicycloheptan-amines. Accordingly, it is an object of the present invention to provide a new method of preparing pharmaceutically active bicycloheptan-amines such as mecamylamine.

SUMMARY OF THE INVENTION

As a first aspect, the present invention provides a process for preparing compounds of Formula I:

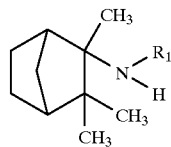

wherein $R_1$ is methyl. The process comprises reducing a compound of the Formula II:

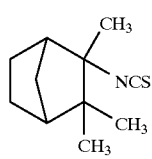

with a reducing agent of the formula:

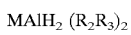

MAlH$_2$ (R$_2$R$_3$)$_2$ wherein M is an alkali metal, and $R_2$ and $R_3$ are each independently alkoxy; to prepare compounds of Formula I. One preferred reducing agent is sodium alanate (i.e., sodium bis(2-methoxyethoxy)aluminum dihydride).

Advantageously, the process of the present invention can be used for preparing pharmaceutically active bicycloheptan-amine compounds including mecamylamine.

The process of the present invention avoids the use of highly reactive species such as lithium aluminum hydride in the reduction reaction, thereby facilitating the commercialization of the process and reducing safety concerns involving the use of lithium aluminum hydride in the workplace.

The foregoing and other aspects of the present invention are explained in further detail in the detailed description and examples set forth below.

DETAILED DESCRIPTION OF THE INVENTION

As used herein, the term "alkyl" refers to $C_{1-8}$ linear, branched, or cyclic, saturated, or unsaturated hydrocarbon chains. Specific examples include but are not limited to methyl, ethyl, ethenyl, propyl, isopropyl, propenyl, isopropenyl, butyl, butenyl, iso-butyl, t-butyl, cyclobutyl, pentyl, cyclopentyl, hexyl, hexenyl, cyclohexyl, octyl, and cyclooctyl.

The term "alkoxy" as used herein refers to $C_{1-8}$ linear, branched or cyclic, oxo-hydrocarbon chains. Specific examples include but are not limited to methoxy, ethoxy, propoxy, isopropoxy, butoxy, iso-butoxy, t-butoxy, pentoxy, and hexyloxy. Methoxy and Ethoxy are preferred.

The bicycloheptan-amine compound of the Formula I:

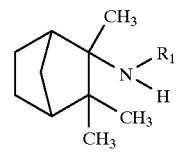

wherein $R_1$ is alkyl, preferably methyl is produced according to the processes of the present invention. When $R_1$ is methyl, the compound of Formula I is mecamylamine.

The compounds of Formula I are produced by the reduction of a isothiocyanato-intermediate of Formula II:

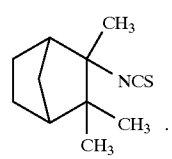

The compounds of Formula II are reduced by reaction with a reducing agent of the Formula:

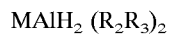

MAlH$_2$ (R$_2$R$_3$)$_2$ wherein M is an alkali metal, $R_2$ and $R_3$ are each independently alkoxy. In one preferred embodiment, $R_2$ is methoxy and $R_3$ is ethoxy. Suitable alkali metals defined by "M" include lithium, sodium, potassium, rubidium, and cesium. Preferred alkali metals are sodium and potassium, more preferably sodium. One particularly preferred reducing agent is sodium alanate which is commercially available under the tradename VITRIDE® from Hexcel Corporation.

The amount of the reducing agent used to effect the reduction of the compounds of Formula II may vary. Typically, the reducing agent is present in an amount sufficient to provide a 2:1 molar ratio of reducing agent: compound of Formula II. The reducing agent may be provided in excess.

The reduction reaction is generally carried out in a solvent. Suitable solvents are known to those skilled in the art and include, for example, ethyl ether, toluene, xylene, and hexane. The reaction is typically carried out at the reflux temperature of the solvent for a period of time sufficient to reduce the compounds of Formula II to the compounds of Formula I. More specifically, the temperature of the reaction is generally between about 55° C. and about 85° C. The reduction reaction is typically carried out for between about 1.5 and about 2 hours.

Previously, the reduction of a cyanatocamphane was not believed to be possible. Conventional methods involved the reduction of a formamidoisocamphane.

The reaction can be easily carried out by solubilizing the reducing agent in the solvent, adding the compound of Formula II and refluxing the reaction. Typically, the product recovered is the free base of the compounds of Formula I. If desired, the free base may be converted to a pharmaceutically acceptable salt by reconstituting the concentrate in a solution saturated with the desired salt. The salt of the compound of Formula I precipitates out of solution and can be recovered and dried.

In this manner, the compound of Formula I may advantageously be provided in the form of a pharmaceutically acceptable salt including but not limited to hydrofluoride salts, hydrochloride salts, hydrobromide salts, hydroiodide salts, methiodide salts, maleate salts, methylsulphonate salts, and fumarate salts.

The compound of Formula II which is reduced to form the compound of Formula I may be produced by a number of methods known to those skilled in the art. The compound of Formula II is typically produced from the camphene starting material which is commercially available. The camphene starting material may be converted to the compound of Formula II by reaction with a potassium thiocyanate.

The reaction of camphene with the cyanating agent is typically carried out in a suitable acidic solvent such as a sulfuric acid or sulfonic acid in glacial acetic acid, using techniques known in the art. For example, suitable techniques are described in U.S. Pat. No. 2,831,027, the disclosure of which is incorporated herein by reference in its entirety. The resulting compound of Formula II is converted to the compound of Formula I using the methods of the present invention.

In one particular embodiment, the present invention provides a process for preparing mecamylamine. The process comprises reacting 2-isothiocyanatoisocamphane with sodium alanate to produce mecamylamine.

The bicycloheptan-amine compounds which is produced according to the methods of the present invention is useful as pharmaceutically active agents. For example, the bicycloheptane-amine compound produced according to the methods of the present invention may be used for the treatment of hypertension in mammalian subjects, including humans. In addition, the bicycloheptan-amine compound produced according to the present invention may be useful as ganglion blockers in mammalian subjects including humans.

The bicycloheptan-amine compound produced according to the present invention may be administered in bulk form for therapeutic treatment. Preferably, the bicycloheptan-amine compounds is formulated into a suitable pharmaceutical formulation for administration to subjects in need thereof. Suitable formulations into which the bicycloheptan-amine compound of the present invention may be incorporated will be readily apparent to those skilled in the art. For example, one preferred formulation includes tablets or capsules including the bicycloheptan-amine produced according to the methods of the present invention together with one or more pharmaceutically acceptable excipients. One preferred formulation for mecamylamine is currently available under the tradename INVERSINE® from Merck & Co.

EXAMPLE 1

2-Isothiocyanatoisocamphane

Potassium thiocyanate (72.9 g, 0.75 moles) suspended into molten dl-camphene (102 g, 0.75 moles) was stirred at 55° C., while a mixture of 48.2 g of conc. sulfuric acid and 18 ml of water was slowly added during 2 hours. The mixture was stirred at 55→85° C. for 5 hours, cooled, and diluted with toluene (300 ml) and water (150 ml). The toluene layer was removed and washed with aqueous sodium bicarbonate solution and water. The toluene solution was anhydrified by means of azeotropic distillation of a portion of toluene. the remaining toluene solution was used for the second step.

EXAMPLE 2

2-Methylaminoisocamphane (Mecamylamine) Hydrochloride

To a 70% toluene solution of sodium alanate (VITRIDE) (430 g), the toluene solution of the first step was added by dropping under stirring at about 55° C. by external cooling. When all the solution was added, the temperature was raised to 85° C. for 1.5 hours.

The whole was cooled at 0° C. and 50 ml of ethyl acetate were dripped maintaining the temperature between 0° and 40° C.

The reaction mixture was then added to a 30% aqueous sodium hydroxide solution (150 ml) diluted with a 5% aqueous sodium hypochlorite solution (750 ml) maintaining the temperature at about 20° C.

The organic layer was removed and washed twice with 100 ml of water and the Mecamylamine was extracted from toluene solution by two washings with diluted hydrochloric acid.

The acid solution was alkalified with 30% aqueous sodium hydroxide solution and the organic base was extracted with hexane. The hexane solution was mixed with isopropanol and acidified with hydrogen chloride gas. The resulting Mecamylamine hydrochloride was filtered and dried to get 96 g (yield 62.9%) of product with m.p. 244–246° C.

The NMR and IR spectra were identical with the U.S. patent reference standard 0172-F-1.

The foregoing is illustrative of the present invention and is not to be construed as limiting thereof. The invention is defined by the following claims, with equivalents of the claims to be included therein.

That which is claimed is:

1. A process for preparing compounds of Formula I:

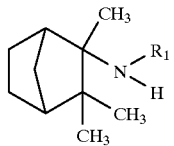

I wherein $R_1$ is methyl;

said process comprising reducing a compound of the Formula II:

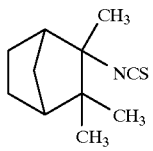

II with a reducing agent of the formula:

$$MAlH_2 (R_2R_3)_2$$

wherein M is an alkali metal, $R_2$ and $R_3$ are each independently alkoxy;

to prepare said compounds of Formula I.

2. The process according to claim 1, wherein M is sodium, $R_2$ is ethoxy, and $R_3$ is methoxy.

3. The process according to claim 1, said process further comprising the step of preparing the compound of Formula II prior to said step of reducing, wherein said step of preparing the compound of Formula II comprises reacting camphene with an alkali metal-thiocyanate.

4. The process according to claim 3, wherein said alkali metal-thiocyanate is potassium thiocyanate.

5. A process for making mecamylamine comprising reducing 2-isothiocyanatoisocamphane with sodium alanate to produce mecamylamine.

* * * * *